United States Patent [19]

Müller

[11] Patent Number: 4,811,693
[45] Date of Patent: Mar. 14, 1989

[54] OBJECT FOR RECEIVING AND STORING USEFUL MEANS

[75] Inventor: Hans-Rudolf Müller, Zürich, Switzerland

[73] Assignee: Züricher Beuteltuchfabrik AG, Ruschlikon, Switzerland

[21] Appl. No.: 14,718

[22] Filed: Feb. 13, 1987

[30] Foreign Application Priority Data

Feb. 18, 1986 [CH] Switzerland .................. 649/86

[51] Int. Cl.⁴ .............................................. A01K 29/00
[52] U.S. Cl. ..................................................... 119/15
[58] Field of Search ........................... 119/15; 43/124; 220/371, 372; 215/248, 308

[56] References Cited

U.S. PATENT DOCUMENTS

| | | | |
|---|---|---|---|
| 1,744,022 | 1/1930 | Davis | 43/124 X |
| 3,140,007 | 7/1964 | Nettleship | 119/15 |
| 3,874,335 | 4/1975 | Galasso | 119/15 X |
| 4,212,267 | 7/1980 | Patterson | 119/15 X |
| 4,250,833 | 2/1981 | Waldon | 119/15 X |

*Primary Examiner*—Robert P. Swiatek
*Attorney, Agent, or Firm*—Helfgott & Karas

[57] ABSTRACT

An article adapted to be dispensed from aircraft onto large surface areas for the purpose of beneficially influencing the environment which employs a hollow casing having at least one opening whereby when at least one item for producing such influence is stored in the casing, the item will be released through the opening to the adjacent surface areas to initiate the influence on the environment after the casing is in landed position. At least one of the items is disposed in the casing. A structural arrangement is secured to the casing to prevent the casing when in landed position from being in direct contact with the surface area, thus shielding the item from the adverse influence of local weather.

12 Claims, 2 Drawing Sheets

OBJECT FOR RECEIVING AND STORING USEFUL MEANS

BACKGROUND OF THE INVENTION

The invention relates to an object or article for receiving and storing useful items, such as materials and the like which are adapted for beneficially influencing the environment as for example being adapted for control and destruction of harmful bacteria and other organisms. The item or items are placed in a hollow casing having an opening.

In an earlier filed U.S. patent application Ser. No. 871,104 use of objects or articles, in which it is possible to place useful items is disclosed. These objects are placed on a ground or base and, after a certain time, the items are released from the object and initiate pest control activity. The objects can also be placed on trees or shrubs, in such positions such that they are protected against the adverse influence of weather and in particular they are protected from rain and moisture.

However, the objects used in this manner must be placed individually into desired position. However, this individual placement is disadvantageous when large numbers of objects are needed and large surface areas must be treated. In order that a large number of objects can be placed in position on large surface areas quickly and easily it is necessary to use aircraft, such as is already known for the purpose of large area pest control using chemical agents.

SUMMARY OF THE INVENTION

The problem of the present invention is to construct such item carrying objects or articles in such a manner that, as in the case of chemical pest control, these objects or articles can be dropped or jettisoned or discharged from the aircraft in large numbers and yet when these articles are disposed in proper position in the surface areas to be treated, the articles will be protected against adverse weather condition.

In accordance with the principles of the invention, an article adapted to be dispensed from aircraft onto large surface areas for the purpose of beneficially influencing the environment employs a hollow casing having at least one opening. When at least one item for producing such influence is stored in said casing, the item will be released through the opening to the adjacent surface areas to initiate said influence after the casing is in landed position. The casing contains at least one of said items. Means secured to said casing has the function of preventing the casing, when in landed position, from being in direct contract with the surface area, thus shielding the item from the adverse influence of local weather. The aforementioned objects and advantages of the invention as well as other objects and advantages thereof will either be explained or will become apparent to those skilled in the art when this specification is read in conjunction with the accompanying drawings and specific description of preferred embodiments which follow.

DETAILED DESCRIPTION OF PREFERRED EMBODIMENTS

Figure 1:
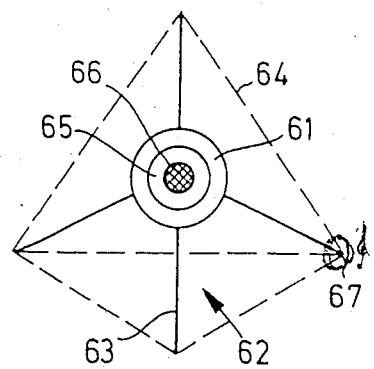
FIG. 1 illustrates an article with a spherical casing in accordance with one embodiment of the invention.

In the drawing:

Similar elements in different embodiments are designated at like reference numerals.

The article shown in FIG. 1 has a casing 61 to whose outer face are fixed projecting support members 62. Support members 62 are e.g. bars 63, which are directed from the center towards the corners of an imaginary tetrahedron 64 shown in broken line form. The article casing 61 is hollow and has a wall 65 containing a plurality of openings 66 with a clearly defined cross-sectional surface. Reference is made to the aforementioned patent specification with regards to additional details of the construction of casing 61 and wall part 65. The bars shown as support member 62 in FIG. 1 can also be constructed as narrow webs or bars with an end plate 67. The function of the support members 62 is to maintain casing 61 independently of the position of the article, in such a way that the casing is not in contact with the ground or base. Such a ground contact would be prejudicial to the useful items housed in the casing 61, if as a result, moisture should enter the interior of the casing. As moisture entry is prevented by the support members 62, it is possible to distribute the articles over large areas by jettisoning from aircraft. Support member 62 reliably prevents any ground contact of casing 61 and therefore damage to the useful items.

Figure 2:
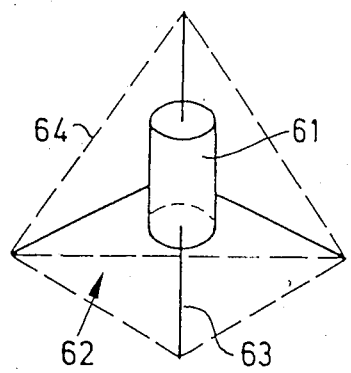
FIG. 2 is a view similar to FIG. 1 but showing a casing with a cylindrical casing.

Whereas in FIG. 1 casing 61 has a hollow spherical shape, the casing 61 of the article according to FIG. 2 is constructed as a hollow cylinder. The support members 62, which are constructed as bars 63, are directed as in FIG. 1 from the center toward the angles or corners of an imaginary tetrahedron 64. Casing 61 also has a wall with clearly defined, not shown openings and the bars 63 can be replaced by other support members 62 ensuring that in all positions casing 61 does not engage the ground after being jettisoned from the aircraft. It is also possible to provide more than four support members 62, but the use of four support members 62 shown in FIGS. 1 and 2 provides an optimum solution with regards to effort and cost. Use of bars 63, prevents articles from being inadvertently hooked together.

Figure 3:
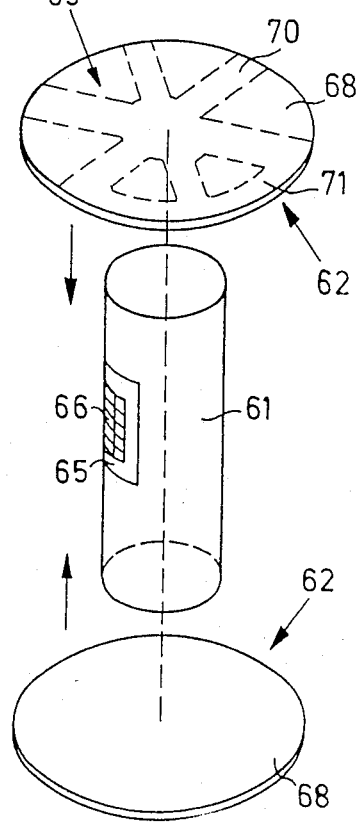
FIG. 3 is an exploded view of an article having a cylindrical casing in accordance with another embodiment of the invention.

In FIG. 3, the article has three parts, namely, a hollow cylindrical casing 61 and two support members 62, which are constructed by foils 68 formed as circular discs. The diameter of the discs is substantially larger than the diameter of the casing. The arrows indicate the assembly of the article with discs 68 covering the end faces of the hollow cylindrical casing. A wall 65 with openings 66 is shown in the circumferential surface of casing 61. The article according to FIG. 3 is also suitable for dropping from aircraft in large quantities and distributing over large areas. There is also a high probability in this case also that the useful means in the casing will not be damaged by moisture. The support members 62 can be shaped in ways other than as disks 68. In one disk 68 in FIG. 3 a disk having spokes is shown as a variant in broken line form and its spokes 70 either have free ends or are held together by a spoke ring 71.

Figure 4:
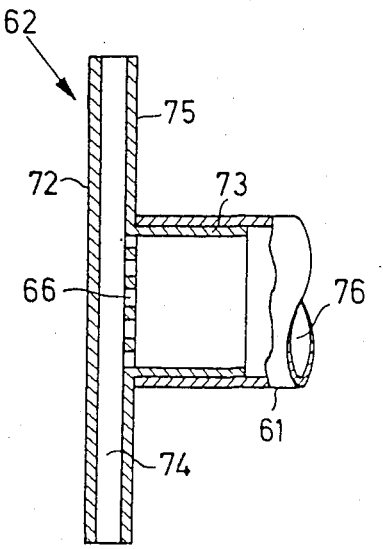
FIG. 4 is a detailed view of a disc used in the article of FIG. 3.

FIG. 4 illustrates an article having two disks 72 (only on of which is shown) as the support member 62. Disk 72 has a bushing 73 in the center thereof and for fitting the article it is placed in the end of the hollow cylindrical casing 61. Disk 72 has a slit-like channel 74 running diagonally there across. Lateral face 75 carrying bushing 73 is provided in the vicinity of the latter with openings 66, through which at the appropriate time the useful items will be released from casing 61. Bushing 73 serves to keep the useful items spaced from support member 62. If on jettisoning from the aircraft the article is dropped in such manner that it lands upon support member 62, i.e. on a disk 72, here again the useful items in the cavity of casing 61 will not be harmed by moisture penetration.

Figure 5:
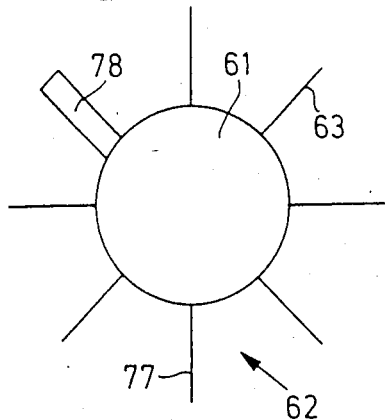
FIG. 5 illustrates an article with a spherical casing in accordance with yet another embodiment of the invention.
Figure 6:
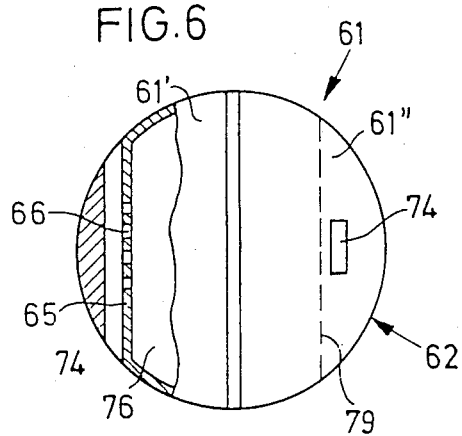
FIG. 6 illustrates an article with a spherical casing in accordance with still another embodiment of the invention.

FIG. 5 shows an article with a spherical casing 61, to whose surface are fixed radially projecting support members 62. The latter can have different forms and can be constructed as bars 63, circular disks 77 or webs 78. However, normally only one of these embodiments is used in an object according to FIG. 5. FIG. 6 shows a hollow spherical casing 61 partially in section. Casing 61 comprises two hemispherical shells 61', 61". It can be seen from the section in the left-hand apart of FIG. 6, that a slit-like channel 74 is provided, which engages a wall portion 65 with openings 66, the latter forming the connection between cavity 76 housing the useful items and the slit-like channel 74. After introducing the useful items, the two casing halves 61', 61" are appropriately assembled in such a way that the channels 74 are at 90° with respect to one another. If, by dropping from aircraft, the articles according to FIG. 6 are also distributed in areas, this embodiment also ensures that in any random position of the article the useful means are not unfavourably influenced or damaged by moisture.

In the construction according to FIG. 6 there are no parts projecting from the outer surface of casing 61, but the spherical segment separated by a broken line 79 in the right-hand part of FIG. 6 forms the support member 62, although it forms a single structure with the particular, casing part 61', 61". However, casing 61 and support member 62 can be separate components.

Figure 7:
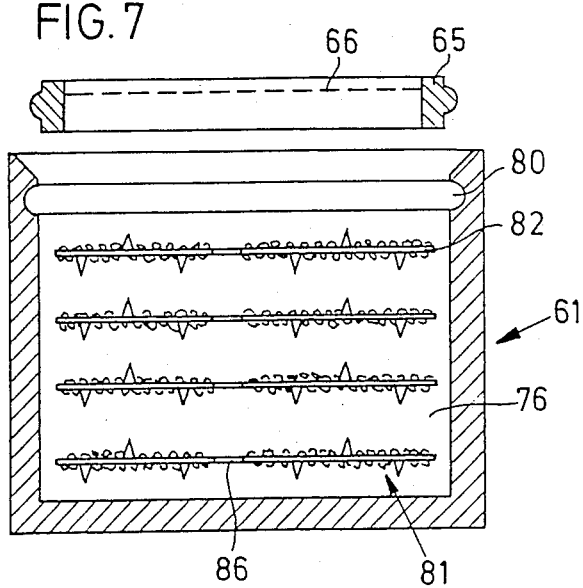
FIG. 7 is a cross sectional view of an article showing items disposed therein.

FIG. 7 shows a hollow cylindrical casing 61 with a wall portion 65 having openings 66. After placing the useful items in the cavity of casing 61, wall portion 65 can be snapped into a slot 80 on the inner wall of casing 61. Support members 62 are arranged in the described manner on casing 61, but are not shown for reasons of simplicity.

Figure 8:
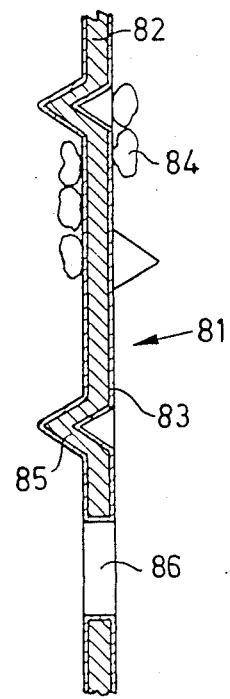
FIG. 8 is a cross sectional view of a portion of the structure shown in FIG. 7.

The housing of the useful items can be as shown in FIGS. 7 and 8. For this purpose use is made of supports 81, e.g. in the form of disks 82, which are coated with an anchoring agent, e.g. an adhesive and then the useful items 84, e.g. eggs, larvae, etc are applied to the disk. In order for the useful items 84 to be properly spaced between the individual disks 82, spacers 85 are arranged on one or both sides of the disks. As shown in FIG. 8, the spacers 85 are impressed into the disks 82, so that the spacers 85 have a conical shape. A passage 86 is provided in the center of each disk 82, so that the useful items 84 can reach the openings 66. The supports 81 for the useful items 84 are stacked in cavity 76 of casing 61, the cavity 76 then being closed by wall part 65. The article formed by casing 61 and support member 62 is then ready to be dropped from the aircraft. The articles according to FIGS. 1 to 6 are prepared in the same way.

Figure 9:
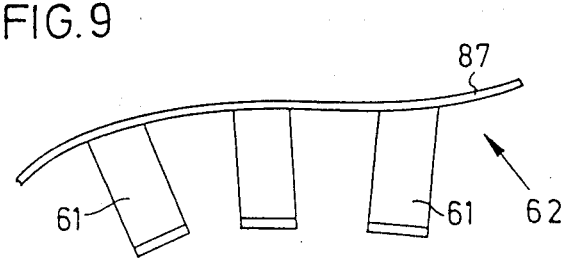
FIG. 9 illustrates yet another embodiment of the invention.

FIG. 9 shows another form of a support member 62, which is constituted by a thread 87, to which casing 61 is fixed in spaced manner. As thread 87 and casing 61 are made from plastic, it is possible to carry out the connection to the thread of string 87 at the same time as producing the casing 61, so that the production of such casing chains is possible with substantially no additional expenditure. By jettisoning from aircraft, such casing chains are preferably distributed over areas in which trees or bushes are growing. The casing chains become caught in branches, which leads to the useful items being protected against moisture.

The special construction of the articles ensures that the useful items can be used in undamaged form, even when dropped from aircraft. The article can be constructed of plastic materials, which have no components prejudicial to the environment and which are degradable after a certain period of time.

While the fundamental novel features of the invention have been shown and described and pointed out, it will be understood that various substitutions and changes in the form of the details of the embodiments shown may be made by those skilled in the art without departing from the concepts of the invention as limited only by the scope of the claims which follow.

What is claimed is:

1. An article adapted to be dispensed from aircraft onto large surface areas for the purpose of beneficially influencing the environment, said article comprising:

a hollow casing having at least one opening whereby when at least one item for producing such influence is stored in said casing, the item will be released through said at least one opening to the adjacent surface areas to initiate said influence after the casing is in landed position; and means secured to said casing to prevent the casing when in landed position from being in direct contact with the surface area, thus shielding the item from the adverse influence of local weather.

2. The article as set forth in claim 1 wherein the means includes at least four support members, each member being secured to the outer surface of the casing and extending from the center thereof toward the corresponding vertices of an imaginary tetrahedron in which the casing is disposed.

3. The article as set forth in claim 2 wherein the casing has a cylindrical shape.

4. The article as set forth in claim 2 wherein the casing has a spherical shape.

5. The article as set forth in claim 1 wherein the means is a thread to which other articles can also be secured.

6. The article as set forth in claim 1 wherein the casing is a cylinder open at both ends and the means includes two parallel discs, each disc closing and sealing a corresponding end of the cylinder, the discs having like diameters which are substantially larger than the diameter of the cylinder.

7. The article as set forth in claim 6 wherein at least one of the discs has a channel extending there across and communicating with the hollow interior of the casing.

8. The article of claim 1 wherein the casing is a sphere and the means is a channel extending across a portion of the sphere with opposite openings flush with the outer surface of the sphere and communicating with the hollow interior of the sphere.

9. The article of claim 1 wherein the means include superimposed laminated disc-like foils.

10. The article of claim 9 wherein the foils have lateral faces with spaced spacer elements for maintaining a minimum spacing between adjacent foils.

11. The article of claim 10 wherein the foils have adhesive coatings on at least one face and the item is secured to said coatings.

12. An article adapted to be dispensed from aircraft onto large surface areas for the purpose of beneficially influencing the environment, said article comprising:

a hollow casing having an internal axis and having first and second ends disposed oppositely at opposite ends of the axis, each of the first and second ends containing an elongated channel having opposite third and fourth open ends and extending at right angles to the axis, each channel having an opening disposed intermediate said third and fourth ends which communicates with the interior of the casing whereby when at least one item for producing such influence is stored in said casing, said at least one item will be released through the openings into the adjacent surface areas to initiate said influence after the casing is in landed position;

said channels constituting means secured to said casing to prevent the interior of the casing when in landed position from being in direct contact with the surface area, thus shielding said at least one item from the adverse influence of local weather.

* * * * *